United States Patent
Kobayashi et al.

(10) Patent No.: US 11,311,572 B2
(45) Date of Patent: Apr. 26, 2022

(54) PREPARATION, METHOD FOR PRODUCING PREPARATION, AND METHOD FOR GENERATING HYDROGEN

(71) Applicants: BOSQUET SILICON CORP., Osaka (JP); KIT Co. Ltd., Osaka (JP)

(72) Inventors: Hikaru Kobayashi, Kyoto (JP); Yuki Kobayashi, Kyoto (JP)

(73) Assignees: BOSQUET SILICON CORP., Osaka (JP); KIT Co. Ltd., Osaka (JP)

(*) Notice: Subject to any disclaimer, the term of this patent is extended or adjusted under 35 U.S.C. 154(b) by 0 days.

(21) Appl. No.: 16/667,477

(22) Filed: Oct. 29, 2019

(65) Prior Publication Data

US 2020/0067554 A1    Feb. 27, 2020

Related U.S. Application Data

(63) Continuation of application No. 16/073,305, filed as application No. PCT/JP2017/000749 on Jan. 12, 2017, now Pat. No. 10,617,712.

(30) Foreign Application Priority Data

Jan. 29, 2016    (JP) .............................. JP2016-015123

(51) Int. Cl.
    *A61K 33/00*        (2006.01)
    *A61K 9/16*         (2006.01)
    (Continued)

(52) U.S. Cl.
    CPC ............ *A61K 33/00* (2013.01); *A61K 9/0007* (2013.01); *A61K 9/14* (2013.01); *A61K 9/1611* (2013.01);
    (Continued)

(58) Field of Classification Search
None
See application file for complete search history.

(56) References Cited

U.S. PATENT DOCUMENTS 10,617,712 B2 *   4/2020   Kobayashi ........... A61K 9/1617
10,617,782 B2     4/2020   Zhang et al.
(Continued)

FOREIGN PATENT DOCUMENTS

CN    102227375 A    10/2011
CN    102741172 A    10/2012
(Continued)

OTHER PUBLICATIONS

Matsuda et al. (Concentration of hydrogen molecules and splitting water using silicon nanoparticles, The 62nd JSAP Spring Meeting Koen Yokoshu, 2015, 11a-A27-6. (Year: 2015).*
(Continued)

*Primary Examiner* — Melissa S Mercier
(74) *Attorney, Agent, or Firm* — Dorsey & Whitney LLP

(57) ABSTRACT

One solid preparation of the present invention mainly includes silicon fine particles, and has a capability of generating hydrogen. In addition, one specific example of the solid preparation mainly includes silicon fine particles having a crystallite diameter principally of 1 nm or more and 100 nm or less, and exhibits a capability of generating hydrogen in an amount of 3 ml/g or more when brought into contact with a water-containing liquid having a pH value of 7 or more. In this solid preparation, hydrogen is generated when the silicon fine particles are brought into contact with a water-containing liquid having a pH value of 7 or more. Therefore, taking advantage of the characteristics of the solid preparation, generation of hydrogen is promoted in, for example, a gastrointestinal tract where the pH value is 7 or
(Continued)

(a)

(b)

more due to secretion of pancreatic fluid after passage through the stomach after oral ingestion.

12 Claims, 6 Drawing Sheets

(51) Int. Cl.
A61K 9/46 (2006.01)
A61K 9/14 (2006.01)
A61K 9/48 (2006.01)
A61P 39/06 (2006.01)
A61K 9/20 (2006.01)

(52) U.S. Cl.
CPC .......... *A61K 9/1617* (2013.01); *A61K 9/1682* (2013.01); *A61K 9/2009* (2013.01); *A61K 9/2013* (2013.01); *A61K 9/485* (2013.01); *A61K 9/4858* (2013.01); *A61P 39/06* (2018.01)

(56) References Cited

U.S. PATENT DOCUMENTS

| | | | |
|---|---|---|---|
| 11,103,527 | B2 | 8/2021 | Kobayashi et al. |
| 2003/0033991 | A1 | 2/2003 | Cheng |
| 2003/0059361 | A1 | 3/2003 | Carberry |
| 2004/0067247 | A1 | 4/2004 | De et al. |
| 2005/0232837 | A1* | 10/2005 | Troczynski ........... H01M 8/065 423/155 |
| 2009/0175985 | A1 | 7/2009 | Canham |
| 2011/0311633 | A1 | 12/2011 | Canham et al. |
| 2012/0034147 | A1 | 2/2012 | Okita |
| 2012/0275981 | A1* | 11/2012 | Foord ..................... C01B 3/065 423/274 |
| 2012/0315684 | A1 | 12/2012 | Hayashi et al. |
| 2013/0098250 | A1 | 4/2013 | Satoh et al. |
| 2014/0377176 | A1 | 12/2014 | Stephan et al. |
| 2015/0258136 | A1 | 9/2015 | Lucas |
| 2016/0200571 | A1 | 7/2016 | Kobayashi et al. |
| 2017/0333518 | A1 | 11/2017 | Uekita et al. |
| 2019/0038664 | A1 | 2/2019 | Kobayashi et al. |
| 2019/0216082 | A1 | 7/2019 | Kobayashi et al. |
| 2019/0231660 | A1 | 8/2019 | Kobayashi et al. |

FOREIGN PATENT DOCUMENTS

| | | |
|---|---|---|
| EP | 1220659 B1 | 9/2004 |
| EP | 1452484 A1 | 9/2004 |
| EP | 2630944 A1 | 8/2013 |
| JP | H0466189 U | 3/1992 |
| JP | 2004115349 A | 4/2004 |
| JP | 2006071330 A | 3/2006 |
| JP | 2006083078 A | 3/2006 |
| JP | 2007521244 A | 8/2007 |
| JP | 2007523096 A | 8/2007 |
| JP | 2008019115 A | 1/2008 |
| JP | 2008247839 A | 10/2008 |
| JP | 2009502157 A | 1/2009 |
| JP | 2009503128 A | 1/2009 |
| JP | 2010045204 A | 2/2010 |
| JP | 2010265158 A | 11/2010 |
| JP | 2011026211 A | 2/2011 |
| JP | 2011506279 A | 3/2011 |
| JP | 2011218340 A | 11/2011 |
| JP | 2011251873 A | 12/2011 |
| JP | 2013199413 A | 10/2013 |
| JP | 2013228319 A | 11/2013 |
| JP | 5514140 B2 | 4/2014 |
| JP | 2014084233 A | 5/2014 |
| JP | 2014193792 A | 10/2014 |
| JP | 2014205635 A | 10/2014 |
| JP | 2014227346 A | 12/2014 |
| JP | 2015113331 A | 6/2015 |
| JP | 2015531363 A | 11/2015 |
| JP | 2016001613 A | 1/2016 |
| JP | 2016152796 A | 8/2016 |
| JP | 2016155118 A | 9/2016 |
| JP | 2017104848 A | 6/2017 |
| JP | 6508664 B1 | 4/2019 |
| JP | 6592725 B2 | 10/2019 |
| KR | 10-1318939 | 10/2013 |
| KR | 101318939 B1 | 11/2013 |
| TW | I295935 | 4/2008 |
| TW | 201126592 A | 8/2011 |
| TW | 201518206 A | 5/2015 |
| WO | 2005046707 A1 | 5/2005 |
| WO | 2005097670 A1 | 10/2005 |
| WO | 2007026533 A1 | 3/2007 |
| WO | 2009071219 A2 | 6/2009 |
| WO | 2010038064 A1 | 4/2010 |
| WO | 2012053472 A1 | 4/2012 |
| WO | 2014049677 A1 | 4/2014 |
| WO | 2015033815 A1 | 3/2015 |
| WO | 2016010139 A1 | 1/2016 |
| WO | 2016129512 A1 | 8/2016 |
| WO | 2017130709 A1 | 8/2017 |

OTHER PUBLICATIONS

Bourzac (Hydrogen Fuel on Demand with Silicon Nanoparticles, Chemical and Engineering News, Jan. 24, 2013. (Year: 2013).*
Loyless et al. (A sodium bicarbonate dosing methodology for pH management in Freshwater-recirculating Aquaculture Systems, pp. 198-205, available online Jan. 9, 2011, Abstract Only (Year: 2011).*
English translation of CN Office Action for Application No. 201780008361.2, dated Apr. 26, 2020.
English translation of IN Office Action for Application No. 201827031149, dated Mar. 20, 2020.
English translation of office action received in Indonesian application No. P00201806006 dated Aug. 24, 2020.
English translation of PCT Publication No. WO 2015/033815 A1 retrieved Jul. 14, 2020.
Machine translation of WO/2015033815 A1, obtained Apr. 26, 2020.
Machine translation of WO/2016010139, obtained Apr. 26, 2020.
"mainly" Merriam-Webster.com. 2019. http://merriam-webster.com (Aug. 6, 2019).
English Translation for Office Action dated Feb. 26, 2019 for Japanese application No. 2018-229323.
English Translation of Notice of Reasons for Refusal received in JP Application No. 2018-535547 dated Jul. 9, 2019.
English Translation of Office Action dated Dec. 4, 2018 for Japanese application No. 2017-563788.
English Translation of Office Action dated Nov. 26, 2018 for Japanese application No. 2017-563788.
English Translation of Shinsuke Matsuda, "Concentration of hydrogen molecules and splitting water using silicon nanoparticle," ISIR Osaka Univ., 2015.
Extended European Search Report for EP Application No. 17743940. 3, dated Jul. 26, 2019.
International Search Report dated Mar. 14, 2017 for PCT Application No. PCT/JP2017/00749, 2 pages.
Kentaro Imamura, etal, "Hydrogen generation from water using Si nanopowder fabricated from swarf", Journal of Nanoparticle Research, vol. 18, No. 5, 2016.
Non-Final office action received in U.S. Appl. No. 16/073,305 dated Aug. 12, 2019.
English Translation of Notification of Reasons for Refusal received in JP Application No. 2019-131994 dated Aug. 13, 2019.
Bourzac, Katherine , "Hydrogen Fuel on Demand with Silicon Nanoparticles," Chemical & Engineering News (Jan. 24, 2013) https://cen.acs.org/content/cen/articles/91/web/2013/01/Hydrogen-Fuel-Demand-Silicon-Nanoparticles.html.
Loyless, Clay J. et al., "A Sodium Bicarbonate Dosing Methodology for pH Management in Freshwater-Recirculating Aquaculture Systems" 59 The Progressive Fish-Culturist 198-205 (1997).

(56) References Cited

OTHER PUBLICATIONS

Matsuda, et al.. "Concentration of Hydrogen Molecules and Splitting Water Using Silicon Nanoparticle", The 62nd JSAP Spring Meeting Koen Yokoshu, Mar. 2015.
Extended European Search Report received in EP App. No. 17843304.1 dated Feb. 7, 2020.
Extended European Search Report received in EP App. No. 17843305.8 dated Feb. 7, 2020.
English translation of Office Action for TW Application No. 106125642, dated Jan. 5, 2021.
English translation for Office Action for JP Application No. 2019-034384, dated Dec. 15, 2020.
English translation of Office Action for IN Application No. 201927007366, dated Dec. 10, 2020.
Office Action for EP Application No. 17743940.3, dated Jan. 12, 2021.
Canham, L T. , "Nanoscale Semiconducting Silicon as a Nutritional Food Additive", Nanotechnology, vol. 18, No. 18, Apr. 2007.
Shabir, Qurrat et al., "Taste and Mouthfeel Assessment of Porour and Non-Porous Silicon Microparticles", Nanoscale Research Letters, vol. 7, No. 1, Jul. 20, 2012, pp. 1-6.
English translation of Office Action for IN Application No. 201927007362, dated Nov. 17, 2020.
English translation of Office Action for IN Application No. 201927007363, dated Oct. 28, 2020.
English translation of Office Action for TW Application No. 106102324, dated Nov. 12, 2020.
English translation for Office Action for TW Application No. 106125643, dated Oct. 6, 2020.
English translation of Office Action for CN Application No. 201780008361.2, dated Sep. 27, 2020.
English translation of Office Action for TW Application No. 106125644, dated Oct. 6, 2020.
English translation of Office Action for TW Application No. 106125642, dated Oct. 7, 2020.
Erogbogbo, Folarin et al., "On-Demand Hydrogen Generation Using Nanosilicon: Splitting Water Without Light, Heat, or Electricity", Nano Letters, vol. 13, published Jan. 14, 2013, pp. 451-456.
English machine translation of PCT Publication No. WO 2017130709 (obtained Jun. 2021).
English Translation for Office Action for JP Application No. 2019-181958, dated Jun. 2, 2021.
English translation of Hearing Notice for Indian Application No. 201827031149, dated Jun. 4, 2021.
English translation of Hearing Notice for Indian Application No. 201927007366, dated May 19, 2021.
English translation of Office Action for Chinese Application No. 201780051862.9, dated May 21, 2021.
English Translation of Office Action for Japanese Application No. 2018-535516, dated May 25, 2021.
English translation of Office Action for Japanese Application No. 2018-535548, dated Jun. 1, 2021.
English translation of Office Action for JP Application No. 2019-181957, dated Jun. 2, 2021.
"Bases—pH Values", obtained online via www.engineeringtoolbox.com, 2021.
"Medical Definition of Quasi", obtained online via www.medicinenet.com, 2021.
Erogbogbo, Folarin et al., "On-Demand Hydrogen Generation Using Nanosilicon: Splitting Water Without Light, Heat, or Electricity", (Including supporting information); Nano Letters, vol. 13, published Jan. 14, 2013.
[English Translation] Brazilian Office Action dated Sep. 21, 2021 for Brazilian Application No. 112018015391-5.
[English Translation] Japanese Office Action dated Aug. 24, 2021 for Japanese Application No. 2021-063404.
[English Translation] Japanese Office Action dated Sep. 14, 2021 for Japanese Application No. 2019-034384.
[English Translation] Taiwanese Office Action dated Aug. 3, 2021 for Taiwanese Application No. 109140194.
[English Translation] Taiwanese Office Action dated Aug. 3, 2021 for Taiwanese Application No. 109140195.
[English Translation] Taiwanese Office Action dated Aug. 4, 2021 for Taiwanese Application No. 110102396.
[English Translation] Taiwanese Second Office Action dated Oct. 4, 2021 for Taiwanese Application No. 109140195.
[English Translation] Final Notification of Reasons for Refusal dated Nov. 30, 2021 for Japanese Application No. 2021-063404.
[English Translation] Notification of Written Opinion on the First Examination dated Oct. 15, 2021 for Chinese Application No. 201780052364.4.
[English Translation] Notification of Written Opinion on the Second Examination dated Oct. 18, 2021 for Chinese Application No. 201780051862.9.
Final Rejection Action received in U.S. Appl. No. 16/327,782 dated Nov. 15, 2021.
Non-Final Rejection received in U.S. Appl. No. 16/327,794 dated Jan. 5, 2022.
[English Translation] Chinese Office Action dated Mar. 11, 2022 for Chinese Patent Application No. 201780051862.9.
[English Translation] Chinese Office Action dated March 3. 2022 for Chinese Patent Application No. 201780051870.3.
[English Translation] Final Notice of Reasons for Refusal dated Mar. 8, 2022 for Japanese Patent Application No. 2019-181958.
[English Translation] Final Notification of Reasons for Refusal dated Feb. 15, 2022 for Japanese Patent Application No. 2018-535516.
[English Translation] Taiwanese Office Action dated Jan. 6, 2022 for Taiwanese Patent Application No. 110104778.
[English Translation] Taiwanese Office Action dated Jan. 17, 2022 for Taiwanese Patent Application No. 109140194.
[English Translation] Taiwanese Office Action dated Jan. 17, 2022 for Taiwanese Patent Application No. 109140195.
[English Translation] Taiwanese Office Action dated Jan. 17, 2022 for Taiwanese Patent Application No. 110131758.
Hearing Notice dated Jan. 21, 2022 for Indian Patent Application No. 201927007362.

* cited by examiner

[Fig. 1]
(a)
(b)

[Fig. 2]
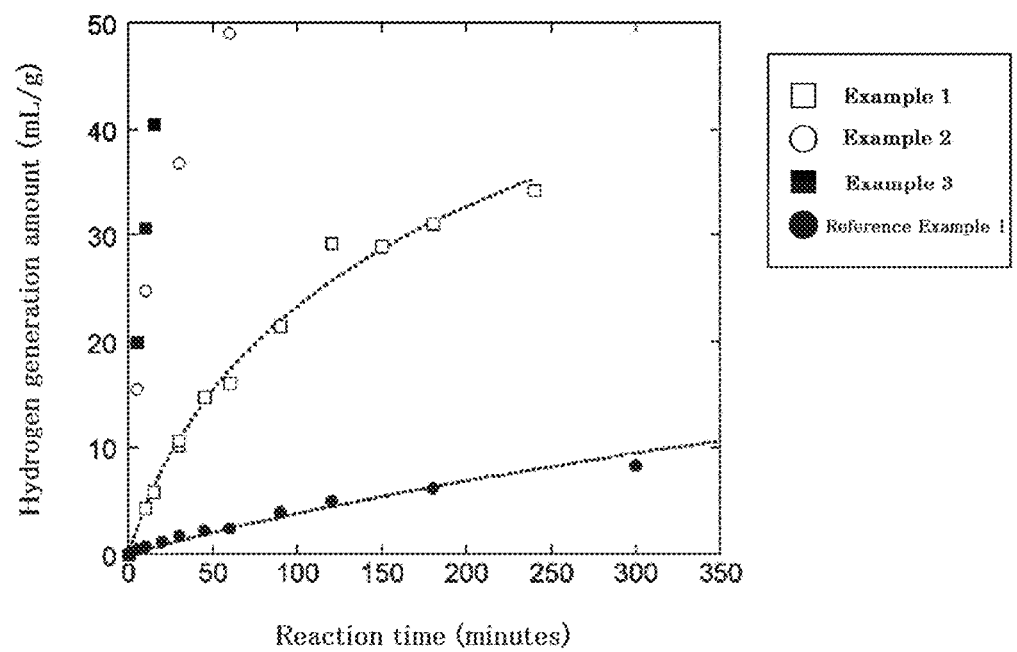

[Fig. 3]

[Fig. 4]
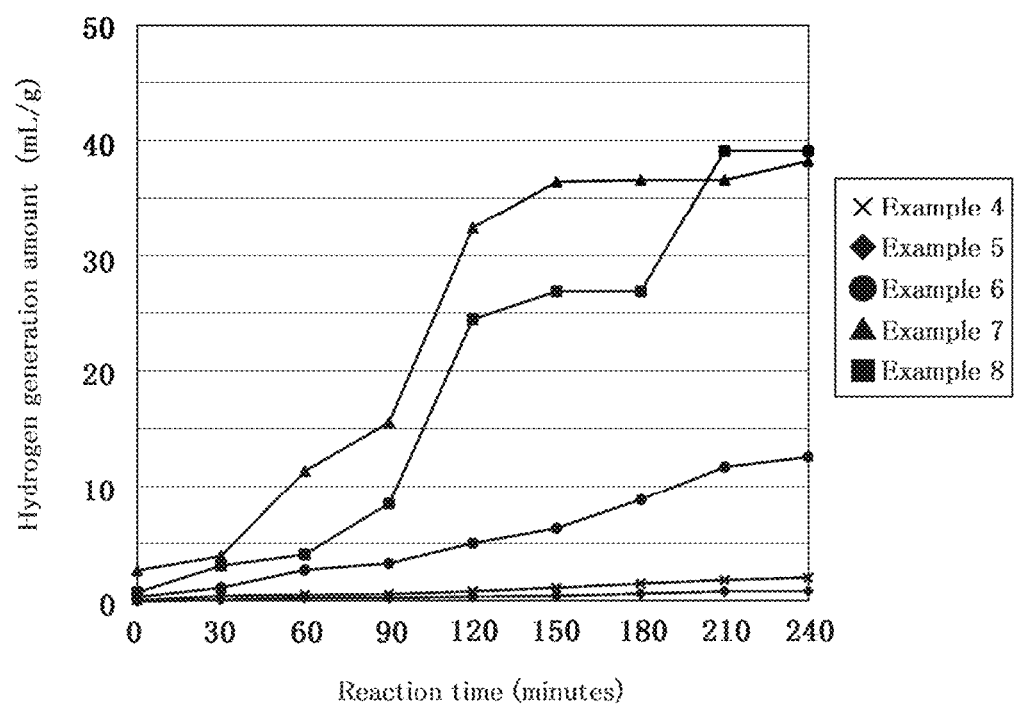

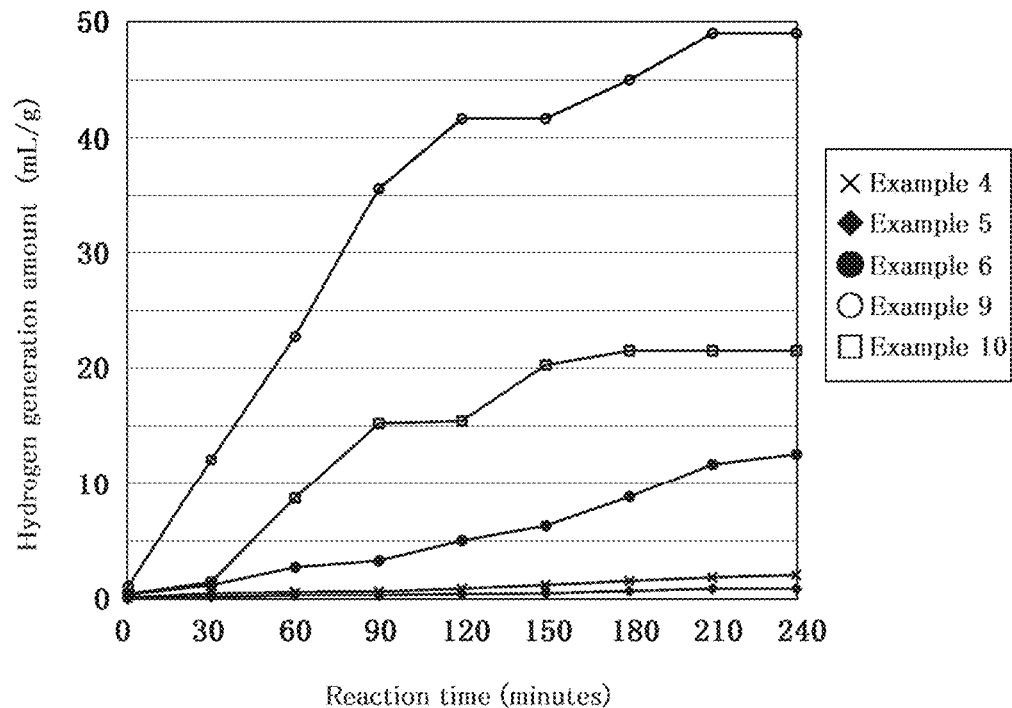
[Fig. 5]
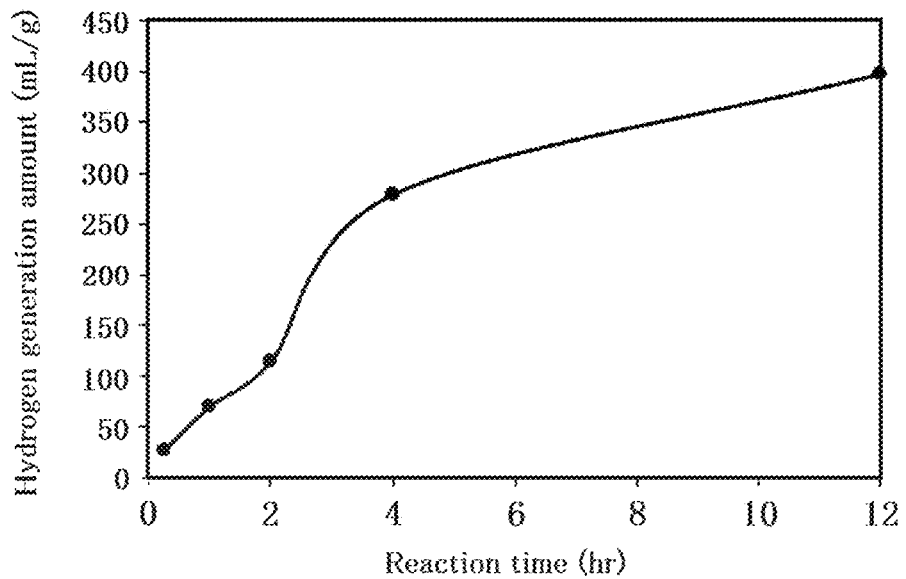
[Fig. 6]

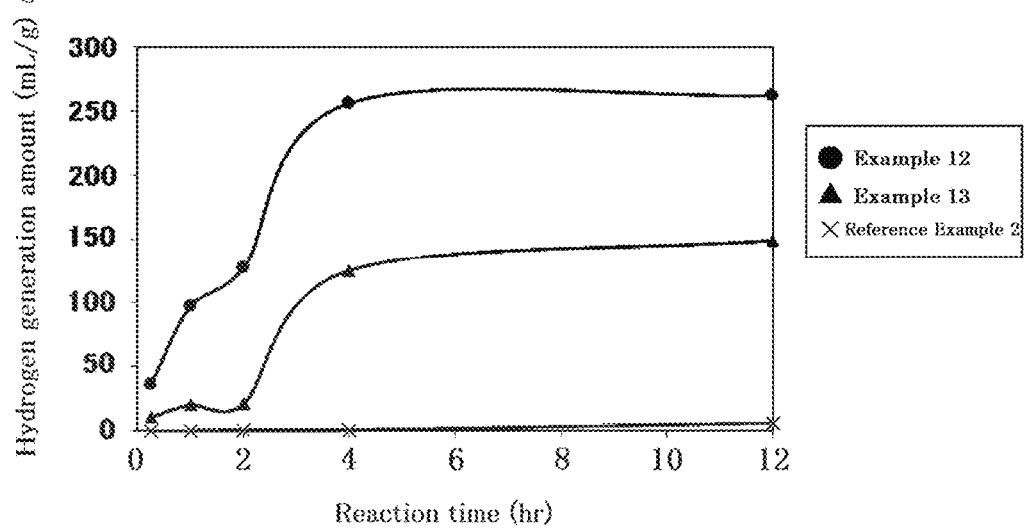
[Fig. 7]

PREPARATION, METHOD FOR PRODUCING PREPARATION, AND METHOD FOR GENERATING HYDROGEN

CROSS-REFERENCE TO RELATED APPLICATION(S)

This application is a continuation of U.S. application Ser. No. 16/073,305 filed Jul. 26, 2018, which is a U.S. National Stage filing under 35 U.S.C. § 371 of PCT Application No. PCT/JP2017/000749, filed Jan. 12, 2017, which claims priority to Japanese Application No. 2016-015123 filed Jan. 29, 2016, which applications are incorporated herein by reference, in their entirety, for any purpose.

TECHNICAL FIELD

The present invention relates to a solid preparation for generating hydrogen, a method for producing the solid preparation, and a method for generating hydrogen.

BACKGROUND ART

Active oxygen derived from oxygen generated in the body and oxygen taken in from the lung is present in a body of an animal such as a human. Active oxygen is known to oxidize and damage cells that form a living body while it is necessary for life support. For example, active oxygen, particularly a hydroxyl radical which has the strongest oxidizing power in active oxygen is considered to cause various diseases such as cancer, stroke, myocardial infarction, diabetes, other lifestyle diseases, and skin disorders such as skin aging and dermatitis. Therefore, it is desirable that excess active oxygen, particularly a hydroxyl radical, which has not been used in a reaction useful for a living body, be prevented from being present in the body wherever possible.

Hydroxyl radicals produced in the body are eliminated by reacting with some substances. Hydrogen is known as an example of substances that eliminate hydroxyl radicals. It is water that is produced by hydrogen reacting with hydroxyl radicals, and water does not produce substances harmful to a living body. Thus, a device for producing hydrogen water containing hydrogen which eliminates hydroxyl radicals in the body has been proposed (e.g. Patent Document 1).

However, hydrogen in hydrogen water is easily diffused into air. Thus, for taking hydrogen in the body in an amount necessary for eliminating hydroxyl radicals, it is necessary that the concentration of dissolved hydrogen in hydrogen water be kept high. Therefore, with a method in which hydrogen water is ingested, it is not easy to take hydrogen in the body in an amount sufficient to react the hydrogen with hydroxyl radicals in the body. Thus, for making to easily take hydrogen in the body, a hydrogen-containing composition containing hydrogen and a surfactant has been proposed (Patent Document 2).

PRIOR ART DOCUMENTS

Patent Documents

Patent Document 1: Japanese Patent Publication No. 5514140

Patent Document 2: Japanese Patent Laid-open Publication No. 2015-113331

SUMMARY OF THE INVENTION

Problems to be Solved by the Invention

However, even when high-concentration hydrogen water is ingested, the amount of hydrogen contained in 1 liter of hydrogen water is only 18 ml in terms of a gas, and in addition, much of hydrogen in hydrogen water is gasified in the stomach and intestines. Thus, there is the problem of causing pneumophagia (so-called "burp") because a sufficient amount of hydrogen is not necessarily taken in the body. On the other hand, when a hydrogen-containing composition with hydrogen encapsulated by a surfactant is ingested, it is necessary to ingest a large amount of the hydrogen-containing composition for taking a sufficient amount of hydrogen in the body. In addition, there may arise the above-mentioned problem that hydrogen is released in the stomach.

The present invention greatly contributes to solving at least one of the above-described technical problems, so that a sufficient amount of hydrogen is easily taken in the body for eliminating hydroxyl radicals in the body. In addition, the present invention can contribute particularly to solving the above-described problem that a hydrogen gas goes out of the body from the inside of the stomach, and easily and efficiently taking hydrogen in the body.

Solutions to the Problems

The present inventors have extensively conducted analysis and studies on silicon fine particles having certain characteristics. Resultantly, the present inventors have found that very interestingly, the silicon fine particles hardly generate hydrogen even when brought into contact with a water-containing liquid (e.g. water or an aqueous solution) having a pH value in a numerical range, but the silicon fine particles may markedly generate hydrogen when brought into contact with a water-containing liquid having a pH value in another numerical range. In addition, it has been found that the generation amount of the hydrogen considerably increases as the pH value increases. In addition, the present inventors have found that by applying the above-mentioned facts, hydrogen can be generated in gastrointestinal tracts after passage through the stomach and after secretion of pancreatic fluid (typically the small intestine and/or the large intestine) while hydrogen is prevented from being generated in the stomach.

A hydrogen generation mechanism using a reaction of silicon fine particles with water molecules is shown in the following formula (1). However, the present inventors have found that the reaction shown in the formula (1) hardly proceeds when silicon fine particles are brought into contact with a water-containing liquid having a low pH value (typically a pH value of less than 7), and the reaction proceeds when silicon fine particles are brought into contact with a water-containing liquid having a pH value of 7 or more (a basic water-containing liquid (hereinafter, referred to as an alkaline water-containing liquid) having a pH value of preferably more than 7, more preferably more than 7.4). The present invention has been made on the basis of the above-mentioned points of viewpoint.

$$Si + 2H_2O \rightarrow SiO_2 + 2H_2 \qquad \text{(Chemical Formula 1)}$$

One solid preparation of the present invention is a solid preparation which mainly includes silicon fine particles, and has a capability of generating hydrogen. A more specific example of a solid preparation mainly includes silicon fine particles having a crystallite diameter principally of 1 nm or more and 100 nm or less, and exhibits a capability of generating hydrogen in an amount of 3 ml/g or more when brought into contact with a water-containing liquid having a pH value of 7 or more.

In this solid preparation, hydrogen is generated when silicon fine particles are brought into contact with the water-containing liquid. In particular, when silicon fine particles are brought into contact with a water-containing liquid having a pH value of 7 or more, a large amount of hydrogen is generated. Therefore, taking advantage of the characteristics of the solid preparation, generation of hydrogen is promoted in, for example, a gastrointestinal tract where the pH value is 7 or more due to secretion of pancreatic fluid after passage through the stomach after oral ingestion. In addition, when the pH value is more than 7 (alkali range in a narrower sense), generation of hydrogen is further promoted. As a result, a large amount of hydrogen can be selectively generated, so to speak, in a specific pH value range. In the present application, the expression of "crystallite" is employed rather than the expression of "crystal grain (or crystal particle)" when the diameter of the crystal is in the "nm order". On the other hand, the expression of "crystal grain (or crystal particle)" is employed when the diameter of the crystal is in the "μm order".

One method for generating hydrogen according to the present invention includes: a first contact step of bringing a solid preparation, which mainly includes silicon fine particles having a crystallite diameter principally of 1 nm or more and 100 nm or less and which exhibits a capability of generating hydrogen in an amount of 3 ml/g when brought into contact with a water-containing liquid having a pH value of 7 or more, into contact with a first water-containing liquid having a pH of less than 7; and a second contact step of bringing the fine silicon particles into contact with a second water-containing liquid having a pH value of 7 or more after the first contact step.

The method for generating hydrogen includes the steps of: bringing the silicon fine particles into contact with the first water-containing liquid having a pH value of less than 7 that is a pH value at which hydrogen is not generated or hardly generated; and bringing the silicon fine particles into contact with the second water-containing liquid having a pH value of 7 or more that is a pH value at which generation of hydrogen is promoted. Thus, it is possible to perform so-called selective generation of hydrogen at a pH value in a specific range. Taking advantage of the characteristics of the method, generation of hydrogen is promoted by bringing the solid preparation into contact with the second water-containing liquid in, for example, a gastrointestinal tract where the pH value is 7 or more due to secretion of pancreatic fluid after passage through the stomach after oral ingestion. In addition, when the pH value of the second water-containing liquid is more than 7 (alkali range in the narrower sense), generation of hydrogen is further promoted.

The method for generating hydrogen can be considered as a method for using the solid preparation when seen from a different angle.

In addition, one method for producing a solid preparation according to the present invention includes the step of finely dividing silicon particles, which have a crystal grain diameter of more than 1 μm, by a bead mill method to obtain silicon fine particles having a crystallite diameter principally of 1 nm or more and 100 nm or less. In addition, the production method is a method for producing a solid preparation which exhibits a capability of generating hydrogen in an amount of 3 ml/g or more when the silicon fine particles are brought into contact with a water-containing liquid having a pH value of 7 or more.

Here, the "silicon fine particles" in the present application include, as main particles, silicon nanoparticles having an average crystallite diameter at a nano level, specifically a crystalline diameter of 1 nm or more and 100 nm or less. In a narrower sense, the "silicon fine particles" in the present application include, as main particles, silicon nanoparticles having an average crystallite diameter at a nano level, specifically a crystalline diameter of 1 nm or more and 50 nm or less. In addition, in the present application, the silicon fine particles include not only those in which silicon nanoparticles are dispersed, but also those in which a plurality of silicon nanoparticles are naturally gathered to form aggregates having a size close to a μm size (generally 0.1 μm or more and 1 μm or less).

In addition, the "water-containing liquid" in the present application is water or an aqueous solution, and encompasses gastrointestinal tract internal fluid of animals (including humans). The "gastrointestinal tract internal fluid" encompasses gastric fluid, pancreatic fluid, and small intestine internal fluid and large intestine internal fluid after secretion of pancreatic fluid. In addition, the material of the "pH adjusting agent" in the present application is not particularly limited as long as it is an agent capable of adjusting the pH value to fall within an alkali range of more than 7.4 (hereinafter, referred to as an "alkali agent"). For example, when the solid preparation is used as an industrial agent, the alkali agent may encompass potassium carbonate, sodium carbonate, sodium hydrogencarbonate, potassium carbonate, sodium hydroxide, potassium hydroxide, and the like. In addition, when the solid preparation is used as an active oxygen neutralizing agent in a living body, an alkali agent recognized as a food additive can be used. The most preferred alkali agent is sodium hydrogencarbonate. Sodium hydrogencarbonate is widely used as a food additive because sodium hydrogencarbonate has a plurality of advantages such that it has a pH value adjustment function required in the present invention, and is excellent in safety and versatility.

In addition, the aspect of the "silicon fine particles" in the present application includes an orally ingestible solid preparation as a state before use. Here, the silicon fine particles can be aggregated in a natural state to form aggregates having a diameter size of μm order (e.g. 1 μm). In the present application, silicon fine particles may be artificially put together by addition of a binding agent, compression or the like to form a lump solid preparation having such a size that it can be picked up by human fingers. The lump solid preparation is sometimes referred to as a "lump preparation" for discriminating the lump solid preparation from the above-mentioned "aggregate". Typical examples of the "lump preparation" include tablets and capsule preparations. The "solid preparation" of the present application encompasses such lump preparations, and further encompasses granular and powdered preparations which assume a powdery form rather than a lump form.

Effects of the Invention

With one solid preparation of the present invention, a large amount of hydrogen is generated from silicon fine particles when the silicon fine particles are brought into contact with a water-containing liquid having a pH value of 7 or more. As a result, a large amount of hydrogen can be generated, so to speak, selectively in a specific pH value range where the pH value is 7 or more.

In addition, one method for generating hydrogen according to the present invention includes the steps of: bringing the silicon fine particles into contact with the first water-containing liquid having a pH value of less than 7 that is a pH value at which hydrogen is not generated or hardly generated; and bringing the silicon fine particles into contact with the second water-containing liquid having a value of 7 or more that is a pH value at which generation of hydrogen is promoted. Thus, hydrogen can be generated, so to speak, selectively at a pH value in a specific range.

BRIEF DESCRIPTION OF THE DRAWINGS

FIG. 1 shows photographs ((a): perspective view and (b): side view) of a solid preparation according to a first embodiment of the present invention.

FIG. 2 is a graph showing the amounts of hydrogen generated in Examples 1 to 3 and Reference Example 1.

FIG. 3 shows a photograph of a state in which the solid preparation according to the first embodiment of the present invention is immersed in pure water for 60 seconds to disintegrate the dosage form.

FIG. 4 is a graph showing hydrogen generation amounts in Examples 4 to 8.

FIG. 5 is a graph showing hydrogen generation amounts in Examples 9 and 10.

FIG. 6 is a graph showing a hydrogen generation amount in Example 11.

FIG. 7 is a graph showing hydrogen generation amounts in Examples 12 and 13 and Reference Example 2.

EMBODIMENTS OF THE INVENTION

Embodiments of the present invention will be described in detail with reference to the accompanying drawings.

[1] Solid Preparation and Method for Producing the Solid Preparation

First Embodiment

A solid preparation of this embodiment is a solid preparation which mainly includes silicon fine particles, and has a capability of generating hydrogen. For the solid preparation of this embodiment, silicon fine particles (hereinafter, sometimes referred to as "silicon nanoparticles" for the sake of convenience) are used which are obtained by finely dividing a commercially available high-purity silicon particle powder (manufactured by Kojundo Chemical Lab. Co., Ltd., particle diameter distribution: <φ 5 μm (typically, silicon particles having a crystal grain diameter of more than 1 μm, purity: 99.9, i-type silicon) as silicon particles by a bead mill method and which include silicon nanoparticles as main particles.

Specifically, 15 g of a high-purity Si powder is dispersed in 300 ml of isopropyl alcohol (IPA) of 99% or more, φ 0.5 μm zirconia beads (volume: 300 ml) are added, and the mixture is finely divided by performing grinding (one-step grinding) at a rotation speed of 2500 rpm for 4 hours using a bead mill apparatus (RMB Badge-Type Ready Mill manufactured by AIMEX CO., Ltd.).

Using a stainless steel material filter (mesh: 0.35 mm) attached to a bead separation container (manufactured by AIMEX CO., Ltd.), silicon nanoparticles including beads are subjected to suction filtration to separate the beads from the silicon nanoparticles. The IPA solution containing silicon nanoparticles separated from the beads is heated to 40° C. using a vacuum evaporator, so that IPA is evaporated to obtain silicon nanoparticles.

The silicon nanoparticles obtained by the above-mentioned method mainly include silicon fine particles having a crystallite diameter principally of 1 nm or more and 100 nm or less. More specifically, as a result of measuring the silicon nanoparticles by an X-ray diffractometer (SMARTLAB manufactured by Rigaku Corporation), the following values were obtained as an example. In a volume distribution, the mode diameter was 6.6 nm, the median diameter was 14.0 nm, and the average crystallite diameter was 20.3 nm.

The silicon nanoparticles were observed using a scanning electron microscope (SEM), and the result showed that the silicon nanoparticles were partially aggregated to form a slightly large formless aggregates of about 0.5 μm or less. In addition, individual silicon nanoparticles were observed using a transmission electron microscope (TEM), many of them had a crystallite diameter of about 2 nm or more and 20 nm or less.

5 mg of the silicon nanoparticles are mixed with 495 mg of a sodium hydrogencarbonate powder (manufactured by Wako Pure Chemical Industries, Ltd., purity: 99.5%). The mixture is kneaded, and formed into a columnar lump body having a diameter of 8 mm and a height of 4 mm by a tableting method, so that a tablet shown in FIG. 1 can be obtained. FIG. 1(a) is a perspective view of a tablet as one example, and FIG. 1(b) is a side view of the tablet as one example. The tablet is one example of a lump preparation as a solid preparation.

Second Embodiment 50 mg of citric acid (manufactured by Wako Pure Chemical Industries, Ltd., purity: 99.5%) is further added to 5 mg of the silicon nanoparticles used in the first embodiment and 495 mg of a sodium hydrogencarbonate powder, and the mixture is kneaded to form a columnar lump body having a diameter of 8 mm and a height of 6 mm, so that the same tablet as the tablet shown in FIG. 1 can be obtained.

Third Embodiment

Except that the amount of citric acid is 200 mg, the same treatment as in the second embodiment is performed to obtain a tablet. This tablet is a columnar tablet similar to the tablet shown in FIG. 1, and has a diameter of 8 mm and a height of 10 mm.

Fourth Embodiment

The silicon nanoparticles described in the first embodiment are immersed in a hydrofluoric acid aqueous solution at a concentration of 5% by mass for 10 minutes. Thereafter, using a fluororesin membrane filter of 100 nm mesh, a filtration treatment in air is performed to trap the silicon nanoparticles on the membrane filter. The membrane filter is held on a fluororesin beaker while the silicon nanoparticles are trapped on the filter. The hydrofluoric acid component is removed by adding ethanol dropwise to the filter held on the beaker. The silicon nanoparticles on the membrane filter from which the hydrofluoric acid component has been removed are dried in air for about 30 minutes. By the above-described procedure, silicon nanoparticles treated with hydrofluoric acid are obtained.

Here, by X-ray photoelectron spectrometry (XPS method), the present inventors measured the thickness of a silicon oxide film on the surfaces of the silicon nanoparticles treated with hydrofluoric acid by the above-described method. Silicon nanoparticles which had not been treated with hydrofluoric acid had a silicon dioxide film having a thickness of about 1.6 nm. On the other hand, when the hydrofluoric acid treatment was performed, the oxide film was removed with high reliability to the extent that the oxide film had a thickness of 0.1 nm or less. Therefore, the silicon nanoparticles treated with hydrofluoric acid had little oxide film.

In the fourth embodiment, silicon nanoparticles from which an oxide film has been removed by the above-described treatment are used in place of the silicon nanoparticles in the first embodiment. A tablet was obtained by carrying out the same procedure as in the second embodiment for other conditions. This tablet is a columnar tablet similar to the tablet shown in FIG. 1, and has a diameter of 8 mm and a height of 4 mm.

Fifth Embodiment 200 mg of the citric acid described in the second embodiment is further added to and mixed with the silicon nanoparticles treated with hydrofluoric acid in the fourth embodiment. Thereafter, the same treatment as in the second embodiment is performed to obtain a tablet. This tablet is a columnar tablet similar to the tablet shown in FIG. 1, and has a diameter of 8 mm and a height of 10 mm.

Sixth Embodiment

The same high-purity silicon particle powder as that used in the first embodiment (typically, silicon particles having a crystal grain diameter of more than 1 μm) is ground in one step in accordance with the procedure described in the first embodiment. Subsequently, using a stainless steel material filter (mesh: 0.35 mm) attached to a bead separation container (manufactured by AIMEX CO., Ltd.), zirconia beads of ϕ 0.5 μm (volume: 300 ml) to be used for one-step grinding are subjected to suction filtration to separate the beads from the silicon nanoparticles. Zirconia beads of 0.3 μm (volume: 300 ml) are added to the silicon nanoparticle-containing solution from which beads have been separated, and the mixture is finely divided by performing grinding (two-step grinding) at a rotation speed of 2500 rpm for 4 hours.

In silicon nanoparticles including beads, the beads are separated from the silicon nanoparticles using a bead separator with a stainless steel material filter (mesh: 0.35 mm) attached thereto. The IPA solution containing silicon nanoparticles separated from the beads is heated to 40° C. using a vacuum evaporator in the same manner as in the first embodiment, so that IPA is evaporated to obtain silicon nanoparticles.

[2] Method for Generating Hydrogen

Seventh Embodiment

Animals are caused to orally ingest the tablets described in the first to fifth embodiments. First, as a first contact step, for example, the tablet is brought into contact with gastric fluid as a first water-containing liquid having a pH value of less than 7 (more specifically, a pH value of about 3 to 4) in the stomach. In addition, for example, the tablet passes through the stomach, and as a second contact step, the tablet is brought into contact with gastrointestinal tract fluid as a second water-containing liquid having a pH value of 7 or more in a gastrointestinal tract after the stomach, specifically the small intestine and/or the large intestine.

Thus, for example, by causing an animal (such as a human) to orally ingest the solid preparation, the silicon nanoparticles (tablet as one more specific example) in each of the embodiments are brought into contact with the first water-containing liquid having a pH value of less than 7 in the first contact step, and brought into contact with the second water-containing liquid having a pH value of 7 or more in the subsequent second contact step, so that hydrogen can be generated in the second contact step. Therefore, the solid preparation containing the silicon nanoparticles of each of the embodiments can exhibit a remarkable capability of generating hydrogen when brought into contact with a water-containing liquid having a pH value of 7 or more.

The tablet in this embodiment is brought into contact with the first water-containing liquid (gastric fluid) in the stomach as the first contact step, and then brought into contact with the second water-containing liquid in a gastrointestinal tract after the stomach (more specifically the small intestine and/or the large intestine). In the gastrointestinal tract after passage through the stomach, secretion of pancreatic fluid causes the second water-containing liquid to has a pH value of 7 or more (in an alkali range in a narrower sense). Thus, it is worth noting that in this embodiment, hydrogen can be generated, so to speak, selectively under such conditions that generation of hydrogen is desired.

Utilization of the above-described action and effect ensures that hydrogen in an amount sufficient to eliminate hydroxy radicals in the body of, for example, an animal (such as a human) can be generated in the intestine with a high absorption rate, and thus easily taken in the body. Particularly in the case of humans, the solid preparation does not generate much hydrogen in the stomach where the pH value is much lower than 7. On the other hand, the solid preparation is disintegrated into a powdery form by passing through the stomach, and reaches the small intestine and/or the large intestine. In the small intestine and/or the large intestine, pancreatic fluid is secreted, and therefore the pH value is in an alkali range of about 7.5 to 8.9, so that the solid preparation generates much hydrogen. This indicates that hydrogen having an antioxidative effect can be more reliably absorbed in the human body (temperature is generally 35° C. or higher and 37° C. or lower).

The example of application of the solid preparation using the silicon nanoparticles described in each of the first to fifth embodiments is not limited to a tablet. For example, even when a capsule preparation with powdery silicon nanoparticles (including those formed into aggregates) encapsulated in a capsule is employed in place of a tablet, the same effect as the above-mentioned effect can be exhibited. As will be described later, silicon nanoparticles can generate much hydrogen when the nanoparticles are in the powdery form having a large surface area rather than being in a lump form, but the nanoparticles are orally ingested easily when formed into a tablet or a capsule preparation. In addition, when the nanoparticles are formed into a tablet or a capsule preparation, they maintain a lump form to some extent, but are increasingly disintegrated to assume a powdery form after passing through the stomach. Thus, in the stomach where it is desired to suppress the hydrogen generation reaction, the surface area of the silicon nanoparticles exposed to gastric fluid and/or gastric contents can be reduced, and in the small intestine and/or large intestine where it is desired to promote the hydrogen generation reaction, the surface area of the silicon nanoparticles exposed to the water-containing liquid can be increased.

In addition, the solid preparation may be a granular preparation. The granular preparation assumes a powdery form in an earlier stage after being orally ingested as compared to tablets and capsules. However, since the pH value of gastric fluid is low (less than 7), the preparation generates little hydrogen even when assuming a powdery form immediately after reaching the stomach, and generates hydrogen in the presence of water after passage through the stomach.

The solid preparation may be a powdered preparation. The powdered preparation is easy to handle when the solid preparation is used as, for example, a constituent component of a food such as a health food, e.g. a food additive. When the solid preparation is used as a food additive, silicon fine particles having a crystallite diameter of 1 nm or more and 100 nm or less may be mixed and used as the solid preparation according to the present invention. Preferably, the silicon fine particles are contained in an amount of 1% by mass or more. The upper limit of the content of silicon fine particles is not specified, but is preferably 40% by mass or less with consideration given to the taste.

In addition, an example of a covering layer applicable to a tablet is a known enteric material hardly soluble in the stomach, which is a coating agent that covers the outermost layer of the tablet. In addition, an example of a covering layer applicable to a capsule preparation is a capsule itself which encapsulates silicon fine particles (mainly aggregates of silicon fine particles), and is produced from a known enteric material hardly soluble in the stomach.

As described above, an example of a solid preparation suitable as an application of the silicon nanoparticles according in this embodiment is a tablet which is a lump preparation which is easily orally ingested in a sufficient amount, or a capsule preparation in which powdery silicon fine particles (including those formed into aggregates) are encapsulated in a capsule. When a tablet is employed, a disintegrating agent may be further included. For the disintegrating agent, a known material can be employed. In addition, a preferred example of a more suitable disintegrating agent is an organic acid, and the most preferred example is citric acid. Here, the organic acid can also function as a binding agent that brings silicon nanoparticles into a lump form.

In addition, the temperature condition of the second water-containing liquid for generation of hydrogen in each of the embodiments is not limited. However, when the temperature of the second water-containing liquid is 35° C. or higher, the hydrogen generation reaction is promoted. The second water-containing liquid is not limited to a liquid in the human body. When the temperature of the second water-containing liquid is 35° C. or higher and 50° C. or lower, generation of hydrogen is promoted with high reliability. However, the upper limit of the temperature of the second water-containing liquid is not limited. For example, when the solid preparation in this embodiment is used as an industrial chemical, the temperature may be higher than 50° C. However, when the temperature becomes higher, there is the problem that equipment (including a container) is required to have high heat resistance, and care is needed for handling. Therefore, the temperature is preferably 100° C. or lower even when the solid preparation is used as an industrial chemical.

EXAMPLES

Hereinafter, the embodiments will be described more in detail by way of examples, but the embodiments are not limited to these examples.

Example 1

First, in Examples 1 to 3 below, silicon nanoparticles themselves are evaluated as preliminary examples without carrying out a tableting process in a tableting method. Specifically, as Example 1, silicon nanoparticles ground in one step were used to conduct an experiment before the silicon nanoparticles were processed into a solid preparation.

10 mg of the silicon nanoparticles described in the first embodiment were added as a powdered preparation (i.e. the silicon nanoparticles were not either mixed with a sodium hydrogencarbonate or kneaded) in a glass bottle having a volume of 100 ml (borosilicate glass having a thickness of about 1 mm, Laborane Screw Tubular Bottle manufactured by AS ONE Corporation.). 30 ml of tap water having a pH value of 7.1 was added in the glass bottle, the glass bottle was hermetically sealed under the temperature condition of a liquid temperature of 25° C., the concentration of hydrogen in the liquid in the glass bottle was measured, and the hydrogen generation amount was determined using the measured hydrogen concentration. For measurement of the hydrogen concentration, a portable dissolved hydrogen meter (Model: DH-35A manufactured by DKK-TOA CORPORATION) was used.

Example 2

In Example 2, the same procedure as in Example 1 was carried out except that potassium hydroxide was dissolved in ultrapure water to set the pH value to 8.0.

Example 3

In Example 3, the same procedure as in Example 1 was carried out except that potassium hydroxide was dissolved in ultrapure water to set the pH value to 8.6.

Reference Example 1

In Reference Example 1, the same procedure as in Example 1 was carried out except that ultrapure water was used in place of tap water, and the pH value of the liquid in the glass bottle was set to 7.0. In addition, in Comparative Example 1 being an example in which a water-containing liquid had a pH value of less than 7, evaluation was performed under the same conditions as in Example 1 except that hydrochloric acid was added as a pH value adjusting agent to ultrapure water to set the pH value to 1.5.

FIG. 2 shows results for hydrogen generation in Examples 1 to 3 that are preliminary examples, and Reference Example 1. The abscissa of the graph represents a time (minutes) during which silicon nanoparticles are immersed in water-containing liquids to be kept in contact with water-containing liquids having various pH values, and the ordinate of the graph represents a hydrogen generation amount. As shown in FIG. 2, it has been found that a large amount of hydrogen can be generated under the condition of a pH value of more than 7. In addition, such an interesting result has been obtained that the hydrogen generation amount per certain time increases as the pH value increases, i.e. the alkalinity becomes stronger. Specifically, in Examples 2 and 3 with a pH value of 8 or more, the hydrogen generation amount was remarkably larger than that in Example 1 with a pH value of less than 8. This indicates that it is preferable to bring the silicon nanoparticles into contact with a water-containing liquid having a pH value of 8 or more because a large amount of hydrogen can be generated in a short time. In Comparative Example 1 (not shown), hydrogen was generated in only a very small amount of 2 ml/g over 5 hours.

Based on the results of the foregoing preliminary examples (Examples 1 to 3), the present inventors performed evaluation shown in each of Example 4 and subsequent examples for the solid preparation processed using the a tableting method.

Example 4

First, as Example 4, one tablet produced through the treatment described in the first embodiment was added in a glass bottle having a volume of 30 ml. 30 ml of pure water (pH value: 7.0) as an example of a water-containing liquid was added in the glass bottle to immerse the tablet in the pure water, and the liquid temperature was kept at 25° C. Under this condition, the glass bottle was hermetically sealed, the hydrogen concentration of hydrogen water generated in the glass bottle was measured using the apparatus described in Example 1, and the hydrogen generation amount was determined.

The tablet gradually lost its shape in the pure water with elapse of time. Specifically, about 60 seconds after the tablet was brought into contact with the pure water, sodium hydrogencarbonate was dissolved in the liquid, and the silicon nanoparticles were partially settled and left on the bottom of the container while being almost uniformly diffused in the liquid as shown in FIG. 3. As a result, the tablet substantially lost its original shape, and assumed a powdery form (or fine powdery form; hereinafter, referred to collectively as a "powdery form") (hereinafter, a phenomenon in which a solid dosage form is disintegrated into a powdery form is referred to as "disintegration". Dissolution of a capsule of a capsule preparation encapsulating a powder also means that a dosage form is disintegrated, and exposure of a powder by dissolution of a capsule is also encompassed in "disintegration"). In this example, sodium hydrogencarbonate released with disintegration of the tablet was dissolved in water, and therefore the pH value of the water-containing liquid in the glass bottle increased to 8.3.

Example 5

Example 5 is an example in which a tablet produced through the treatment described in the second embodiment was used. The tablet was almost wholly disintegrated into a powdery form about 5 minutes after being brought into contact with pure water under the temperature condition of a liquid temperature of 25° C. In the process of disintegration of the tablet (i.e. until 90 minutes after the tablet is brought into contact with pure water), sodium hydrogencarbonate and citric acid are released with disintegration of the tablet, so that the water-containing liquid has a pH value of 8.6.

Example 6

In Example 6, the tablet prepared in accordance with the procedure described in the third embodiment was used as a tablet. The tablet was almost wholly disintegrated into a powdery form about 5 minutes after being brought into contact with pure water under the temperature condition of a liquid temperature of 25° C. In the process of disintegration of the tablet (i.e. until 90 minutes after the tablet is brought into contact with pure water), sodium hydrogencarbonate and citric acid are released with disintegration of the tablet, so that the water-containing liquid has a pH value of 8.2.

Example 7

In Example 7, the tablet prepared in accordance with the procedure described in the second embodiment was used as a tablet. In addition, the glass bottle was held in a thermostatic bath to keep the water temperature at 37° C. As the water-containing liquid, pure water having a pH value of 7.0 was used. The tablet was almost wholly disintegrated into a powdery form about 5 minutes after being brought into contact with pure water. Sodium hydrogencarbonate and citric acid are released with disintegration of the tablet, so that the water-containing liquid has a pH value of 8.6.

Example 8

In Example 8, the tablet prepared in accordance with the procedure described in the third embodiment was used as a tablet. In addition, the glass bottle was held in a thermostatic bath to keep the water temperature at 37° C. As the water-containing liquid, pure water having a pH value of 7.0 was used. The tablet was almost wholly disintegrated into a powdery form about 5 minutes after being brought into contact with pure water. Sodium hydrogencarbonate and citric acid are released with disintegration of the tablet, so that the water-containing liquid has a pH value of 8.3.

FIG. 4 shows results in Examples 4 to 8. In FIG. 4, the abscissa represents a time (minutes) during which the tablet is kept in contact with the water-containing liquid, and the ordinate of the graph represents a hydrogen generation amount.

In Example 4, the dosage form of the tablet was disintegrated as shown in FIG. 3, so that sodium hydrogencarbonate was released. In addition, as shown in FIG. 4, the hydrogen generation amount increased with elapse of the contact time between the tablet and the water-containing liquid.

In addition, comparison of Example 5 with Example 7 and comparison of Example 6 with Example 8 showed that the hydrogen generation amount increased under the temperature condition of 37° C. close to the body temperature. Specifically, it is worth noting that in Examples 7 and 8, it was confirmed that hydrogen was generated in an amount of 20 ml/g or more in 150 minutes (two and a half hours).

Further, comparison between results in Examples 1 to 3 in which silicon nanoparticles were brought into contact with the water-containing liquid while being in a powdery form and results in Examples 4 to 6 in which silicon nanoparticles were used as the solid preparation shows that a larger amount of hydrogen can be generated when the silicon nanoparticles are brought into contact with the water-containing liquid while being in a powdery form. However, powdery silicon fine particles are difficult to orally ingest and deliver into the gastrointestinal tract. Thus, in this example, the silicon fine particles are formed into a solid preparation such as a tablet or a capsule preparation. As shown in FIG. 3, the solid preparation is disintegrated into a powdery form when kept in contact with the water-containing liquid for a certain time. Thus, the solid preparation in this example is suitably used such that the solid preparation is kept in contact with a water-containing liquid which does not actively generate hydrogen and which has a pH value of less than 7, so that disintegration of the solid preparation is promoted, and the solid preparation in a powdery form to some extent is brought into contact with a water-containing liquid having a pH value of 7 or more, preferably more than 7.4, more preferably 8 or more, so that generation of hydrogen is promoted.

Example 9

In Example 9, the tablet prepared in accordance with the procedure described in the fourth embodiment was used as a tablet. As the water-containing liquid, pure water having a pH value of 7.0 was used. The tablet was almost wholly disintegrated into a powdery form about 5 minutes after being brought into contact with pure water, and the water-containing liquid had a pH value of 8.6.

Example 10

In Example 10, the tablet prepared in accordance with the procedure described in the fifth embodiment was used as a tablet. As the water-containing liquid, pure water having a pH value of 7.0 was used. The tablet was almost wholly disintegrated into a powdery form about 5 minutes after being brought into contact with pure water, and the water-containing liquid had a pH value of 8.2.

FIG. 5 shows results in Examples 9 and 10. In addition, for facilitating comparison, the results in Examples 4 to 6 are also shown. In addition, the abscissa of the graph represents a time (minutes) during which the tablet is kept in contact with the water-containing liquid, and the ordinate of the graph represents a concentration of hydrogen in the glass bottle. Specifically, it is worth noting that in Examples 9 and 10, it was confirmed that hydrogen was generated in an amount of 20 ml/g or more in 150 minutes (two and a half hours).

Example 11

As Example 11, generation of hydrogen by reaction of silicon nanoparticles with water was observed using surface-treated silicon nanoparticles in place of the silicon nanoparticles in Example 1. Specifically, 2.5 mg of the silicon nanoparticles described in the fourth embodiment were added in the same glass bottle as that used in Example 1. 110 ml of water having a sodium hydrogencarbonate concentration of 0.03% by mass and a pH value of 8.4 was added in the glass bottle to eliminate void portions, the glass bottle was hermetically sealed under the temperature condition of a liquid temperature of 37° C., the concentration of hydrogen in the liquid in the glass bottle was measured, and the hydrogen generation amount was determined using the measured hydrogen concentration. Measurement of the hydrogen concentration was performed in the same manner as in Example 1.

In this example, 397 ml (milliliters) of hydrogen per 1 g of silicon nanoparticles was generated by the reaction for 12 hours as shown in FIG. 6. This hydrogen generation amount corresponds to the amount of hydrogen contained in 22 l (liters) of saturated hydrogen water having a hydrogen concentration of 1.6 ppm. It is worth noting that such an extremely large amount of hydrogen is generated even after a long period of time (e.g. after 12 hours).

Example 12

In Example 12, silicon nanoparticles obtained by grinding silicon particles in two steps were used as a solid preparation. Specifically, silicon nanoparticles ground in two steps in accordance with the procedure described in the sixth embodiment were obtained.

The obtained silicon nanoparticles were measured by an X-ray diffractometer (SMARTLAB manufactured by Rigaku Corporation). Resultantly, in a volume distribution, the mode diameter was 5.8 nm, the median diameter was 9.6 nm, and the average crystallite diameter was 12.2 nm.

2.5 mg of silicon nanoparticles ground in two steps in accordance with the above-described procedure was added in a 100 ml-volume glass bottle similar to that in Example 11. 110 ml of water having a sodium hydrogencarbonate concentration of 0.03% by mass and a pH value of 8.4 was added in the glass bottle, the glass bottle was hermetically sealed under the temperature condition of a liquid temperature of 37° C., the concentration of hydrogen in the liquid in the glass bottle was measured, and the hydrogen generation amount was determined using the measured hydrogen concentration. Measurement of the hydrogen concentration was performed in the same manner as in Example 1.

Example 13

In addition, an experiment was conducted under the same conditions as in Example 12 except that in place of silicon nanoparticles ground in two steps, silicon nanoparticles ground in one step, i.e. the same silicon nanoparticles as those used in Example 1, were used as a solid preparation.

Reference Example 2

As Reference Example 2, an experiment was conducted under the same conditions as in Example 12 except that in place of silicon nanoparticles, silicon particles that were not finely divided, i.e. silicon particles having a diameter of 5 μm, were used.

FIG. 7 shows results in Examples 12 and 13, and Reference Example 2. The results in Examples 1 and 12 showed that even silicon nanoparticles that are not subjected to a surface treatment generated hydrogen. In addition, when silicon nanoparticles ground in two stages were reacted for 12 hours, the hydrogen generation amount was 262 ml per 1 mg of silicon nanoparticles, which was larger than the hydrogen generation amount (149 ml) with silicon nanoparticles ground in one step. On the other hand, for silicon particles which were not finely divided, and did not have a particle diameter in a nanometer order, the hydrogen generation amount with a reaction time of 12 hours was only 4.8 ml. These experiments showed that the hydrogen generation amount increased as the crystallite diameter of silicon nanoparticles decreased. It is worth noting that in any of the above-described examples, hydrogen is continuously generated for at least 12 hours.

As described above, a solid preparation containing silicon fine particles at least partially assume a powdery form, and can generate hydrogen in a water-containing liquid having a pH value of 7 or more. The solid preparation is orally administered to enter gastrointestinal tracts including the stomach and the intestines in an animal, and is gradually disintegrated by passing the inside of the stomach under a so-called acidic condition with a pH value of less than 7. In the gradually disintegrated solid preparation (including disintegrated products thereof), generation of hydrogen is promoted to generate a large amount of hydrogen in the small intestine and subsequent tracts where pancreatic fluid is secreted, and the pH value is in an alkali range of more than 7 (particularly, an alkali range of more than 7.4). The upper limit of the pH value is not particularly limited, but for example, considering that the pH value as a bath salt is preferably in a range of 11 or less, and the pH value as potable water is preferably in a range of 9 or less, the pH value is preferably less than 11.

Therefore, for example, the solid preparation in each of the embodiments or each of the examples suppresses generation of a hydrogen gas in the stomach, and generates a large amount of hydrogen after passing through the stomach. Thus, according to each of the embodiment or each of the examples, hydrogen necessary for educing active oxygen or eliminating active oxygen in the body while suppressing generation of a hydrogen gas in the stomach is supplied in the small intestine and subsequent tracts. As a result, the solid preparation in each of the embodiments or each of the examples can greatly contribute to reduction of active oxygen or elimination of active oxygen.

One aspect of the method for producing a solid preparation includes the step of finely dividing silicon particles having a crystal grain diameter of more than 1 μm by a physical grinding method, so that the silicon particles are formed into silicon fine particles having a crystallite diameter principally of 1 nm or more and 100 nm or less. The solid preparation obtained by the production method mainly includes silicon fine particles, and exhibits a capability of generating hydrogen in an amount of 3 ml/g or more when the silicon fine particles are brought into contact with a water-containing liquid having a pH value of 7 or more. In one preferred aspect of the production method, the silicon fine particles form a main component of the solid preparation. In addition, a preferred example of a physical grinding method is a method for grinding particles by a bead mill grinding method, a planetary ball mill grinding method, a jet mill grinding method, or a combination of two or more thereof. However, from the viewpoint of production cost or ease of production control, a particularly preferred example is only a bead mill grinding method or a grinding method including at least a bead mill grinding method.

In each of the embodiments and examples, a tablet is employed as one example of the solid preparation, but the target in each of the embodiments and examples is not limited to the tablet. Even when other "lump preparation" (e.g. capsule preparation), or solid preparations such as granular and powdered preparations which assume a powdery form rather than a lump form, i.e. one other example of a solid preparation, is employed, at least a part of the effect of each of the embodiments and examples can be exhibited.

In each of the embodiments, isopropyl alcohol (IPA) is used for finely dividing the Si powder in the bead mill apparatus, but the type of liquid for dispersing the Si powder in finely dividing the Si powder is not limited to isopropyl alcohol (IPA). For example, even when ethanol (e.g. 99.5 wt %) is employed in place of isopropyl alcohol (IPA), the same effect as the effect based on the first embodiment can be exhibited. In addition, in the fourth embodiment, a hydrofluoric acid aqueous solution is used, but the liquid in which silicon nanoparticles are immersed in the fourth embodiment is not limited to a hydrofluoric acid aqueous solution. For example, by immersing silicon nanoparticles for about 30 minutes in a hydrogen peroxide solution (e.g. 100 mL of 3.5 wt % hydrogen peroxide water contained in a Pyrex (registered trademark) glass container and heated to about 75° C.) in place of a hydrofluoric acid aqueous solution, the same effect as the effect based on the fourth embodiment can be exhibited. As described above, use of ethanol and/or hydrogen peroxide water is one preferred aspect in that hydrogen can be generated by using a safer and more secure material (e.g. having less influence on the human body).

INDUSTRIAL APPLICABILITY

The solid preparation of the present invention can also be used as food for rearing for rearing animal, food animals, animals for medical use, fish for culturing or the like. Further, the solid preparation can be used as an industrial chemical or agent. The solid preparation can also be used as a human supplement or food additive.

The invention claimed is:

1. A preparation comprising an aggregate of silicon fine particles having a silicon dioxide film having a thickness of 1.6 nm or less, wherein the aggregate has a size of 0.1 μm or more, and wherein the aggregate has a capability of generating hydrogen when the aggregate contacts a gastrointestinal tract internal fluid in a small intestine or subsequent tract, wherein the preparation is orally ingestible.

2. The preparation according to claim 1, further comprising an organic acid.

3. The preparation according to claim 1, which is a capsule preparation in which the silicon fine particles are encapsulated, or a tablet formed so that the silicon fine particles are in a lump form.

4. The preparation according to claim 1, comprising a covering layer which is hardly soluble in a stomach, and is dissolved in the small intestine and/or the large intestine.

5. A method for producing a preparation comprising an aggregate of silicon fine particles having a silicon dioxide film having a thickness of 1.6 nm or less, the method comprising the step of finely dividing silicon particles having a crystal grain diameter of more than 1 μm by a physical grinding method, so that the silicon particles are formed into silicon fine particles and the aggregates of silicon fine particles,
    the aggregate of silicon fine particles exhibiting the capability of generating hydrogen when the aggregate of silicon fine particles contacts a gastrointestinal tract internal fluid in a small intestine or subsequent tract, wherein the preparation is orally ingestible, and wherein the aggregate of silicon fine particles has a size of 0.1 μm or more.

6. The method for producing a preparation according to claim 5, wherein the physical grinding method is selected from a bead mill grinding method, a planetary ball mill grinding method, a jet mill grinding method, and a combination thereof.

7. A method for generating hydrogen, the method comprising:
    a first contact step of bringing a preparation, which comprises an aggregate of silicon fine particles having a silicon dioxide film having a thickness of 1.6 nm or less, the aggregate exhibits the capability of generating hydrogen when the aggregate contacts a gastrointestinal tract internal fluid in a small intestine or subsequent tract, wherein the preparation is orally ingestible, and wherein the aggregate has a size of 0.1 μm or more; and
    a second contact step of bringing the fine silicon particles into contact with a second water-containing liquid having a pH value of 7 or more after the first contact step.

8. The method for generating hydrogen according to claim 7, wherein the preparation is brought into contact with the second water-containing liquid at 35?C or higher and 45?C or lower.

9. The method for generating hydrogen according to claim 7, wherein the preparation is brought into contact with the second water-containing liquid having a pH value of 8 or more.

10. The method for generating hydrogen according to claim 7, wherein the preparation is one selected from the group consisting of a capsule preparation in which the silicon fine particles are encapsulated, and a tablet formed so that the silicon fine particles are in a lump form.

11. The method for generating hydrogen according to claim 7, the method further comprising the step of causing a rearing animal to ingest the preparation,
   the preparation being disintegrated in gastrointestinal tracts of the rearing animal.

12. The preparation according to claim 1, further comprising a binding agent configured to bring the silicon fine particles into a lump form for oral ingestion.

\* \* \* \* \*